(12) United States Patent
Bhattacharya et al.

(10) Patent No.: US 11,059,848 B2
(45) Date of Patent: Jul. 13, 2021

(54) ARTEMISINIC ACID GLYCOCONJUGATE COMPOUNDS, PROCESS FOR PREPARATION AND USE THEREOF

(71) Applicant: Council of Scientific and Industrial Research, New Delhi (IN)

(72) Inventors: Asish Kumar Bhattacharya, Maharashtra (IN); Tharun Kumar Kotammagari, Maharashtra (IN); Manas Kumar Santra, Maharashtra (IN)

(73) Assignee: Council of Scientific and Industrial Research

( * ) Notice: Subject to any disclaimer, the term of this patent is extended or adjusted under 35 U.S.C. 154(b) by 0 days.

(21) Appl. No.: 16/958,997

(22) PCT Filed: Jan. 3, 2019

(86) PCT No.: PCT/IN2019/050006
§ 371 (c)(1),
(2) Date: Jun. 29, 2020

(87) PCT Pub. No.: WO2019/135257
PCT Pub. Date: Jul. 11, 2019

(65) Prior Publication Data
US 2020/0331953 A1    Oct. 22, 2020

(30) Foreign Application Priority Data
Jan. 3, 2018 (IN) ............................ 201811000290

(51) Int. Cl.
*C07H 19/056* (2006.01)
*A61P 35/00* (2006.01)
*C07H 1/00* (2006.01)

(52) U.S. Cl.
CPC ............ *C07H 19/056* (2013.01); *A61P 35/00* (2018.01); *C07H 1/00* (2013.01)

(58) Field of Classification Search
CPC .......... C07H 19/056; C07H 1/00; A61P 35/00
USPC ....................................................... 514/43
See application file for complete search history.

(56) References Cited

FOREIGN PATENT DOCUMENTS

| WO | WO2008065370 A2 | 6/2008 |
| WO | WO2009093007 A2 | 7/2009 |

OTHER PUBLICATIONS

PCT International Search Report and Written Opinion issued by the International Bureau for PCT Application No. PCT/IN2019/050006, dated Mar. 14, 2019, pp. 1-8.
Beckmann et al., "Azides in carbohydrate chemistry," Organic Azides: Syntheses and Applications, pp. 469-490, 2010.
Kawamoto et al., "Biotransformation of artemisinic acid by cultured cells of aremisia annua," Phytochemistry, 48(8): 1329-1333, 1998.
Schneider et al., "Synthesis of New Family of Thiazoline and Thiazole Esters and Investigation of Their Thermal Properties," J. Braz. Chem. Soc., 25(8):1493-1503, 2014.
Zhu et al., "Region-selective biosynthesis of artemisinic acid glycosides by crown galls of Panax quinquefolium and their in vitro antitumor activities," Pharmacognosy Magazine, 11(43):518-523, Jul.-Sep. 2015.

*Primary Examiner* — Shaojia A Jiang
*Assistant Examiner* — Michael C Henry
(74) *Attorney, Agent, or Firm* — Belles Katz LLC

(57) ABSTRACT

The present invention relates to artemisinic acid glycoconjugate compounds. More particularly, the present invention relates to a glycoconjugate compound of formula (I) and a process for the preparation of artemisinic acid glycoconjugate compound of formula (I) by using 1,3-dipolar cycloaddition chemistry starting from artemisinic acid.

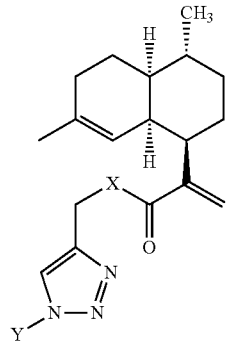

Formula (I)

10 Claims, No Drawings

ARTEMISINIC ACID GLYCOCONJUGATE COMPOUNDS, PROCESS FOR PREPARATION AND USE THEREOF

CROSS-REFERENCE TO RELATED APPLICATIONS

This application is a National Stage of International Application No. PCT/IN2019/050006, filed Jan. 3, 2019, which claims the benefit of Indian Application No. 201811000290, filed on Jan. 3, 2018. The disclosures of the above applications are incorporated herein by reference.

FIELD OF THE INVENTION

The present invention relates to artemisinic acid glycoconjugate compounds. More particularly, the present invention relates to a glycoconjugate compound of formula (I) and a process for the preparation of artemisinic acid glycoconjugate compound of formula (I) by using 1,3-dipolar cycloaddition chemistry starting from artemisinic acid.

BACKGROUND AND PRIOR ART OF THE INVENTION

Artemisinin is a component of the traditional Chinese medicinal herb *Artemisia annua*, which has been utilized for controlling symptoms of fever in China for over 1000 years. Artemisinic acid (AA), which has a similar chemical structure (cadinane-type sesquiterpene) to that of artemisinin, is widely investigated as a presumed intermediate in the biosynthetic pathway of artemisinin in *A. annua*. Artemisinic acid is a putative biogenetic precursor for the synthesis of artemisinin. Artemisinic acid has been reported to be more abundant than artemisinin in the leaves of *A. annua* (Kawamoto H, Asada Y, Sekine H, Furuya T. *Phytochemistry*, 1998, 48, 1329.) Biotransformation of artemisinic acid produces artemisinic acid glycosides, which showed strong activity against Hela cell lines (Zhu J, Chen L, Hu X, Song L, Wang M, Yu R, *Pharmacogn Mag.* 2015, 11, 518).

Article titled "Synthesis of New Family of Thiazoline and Thiazole Esters and Investigation of their Thermal Properties" by Juliana M. F. M. Schneider et al. published in *Journal of the Brazilian Chemical Society*, 2014, Vol. 25, No. 8, 1493-1503 reports Thiazoline esters were obtained by cyclization reaction from 4-substituted benzenenitrile and amino acid L-cysteine followed by esterification reaction with selected alcohols and phenol.

Article titled "Azides in Carbohydrate Chemistry" by Henning S. G. Beckman published in *Organic Azides: Syntheses and Applications*, 2010, 469-490 reports synthesis of Glycoconjugates via Azide-Alkyne [3+2] Cycloaddition. The copper (I)-catalyzed azide-alkyne cycloaddition (CuAAC) enables the regioselective formation of 1,4-di substituted 1,2,3-triazoles under very mild conditions even in a biological context. However, the cellular toxicity of the copper catalyst precludes applications wherein cells must remain viable.

There is no report in the prior art for the organic synthesis of artemisinic acid derivatives. The prior art reports only biosynthesis of artemisinic acid glycosides. Considering the biological importance of the artemisinic acid or derivatives thereof there is need to develop the organic synthesis of artemisinic acid derivatives.

OBJECTIVES OF THE INVENTION

The main objective of the present invention is to provide an artemisinic acid glycoconjugate compound of formula (I).

Another objective of the present invention is to provide a process for the preparation of artemisinic acid glycoconjugate compound of formula (I).

Yet another objective of the present invention is to provide a pharmaceutical composition comprising artemisinic acid glycoconjugate compound of formula (I) and at least one pharmaceutically acceptable carrier.

Still another objective of the present invention is to provide use of artemisinic acid glycoconjugate compound of formula (I) as anti-cancer agent, anti-fungal agent, antimalarial agent, antipyretic agent, antibacterial agent, or imaging agent. Further, the present invention provides artemisinic acid glycoconjugate compound of formula (I) which shows allelopathy effect or anti-adipogenesis effect.

SUMMARY OF THE INVENTION

Accordingly, the present invention provides an artemisinic acid glycoconjugate compound of formula (I);

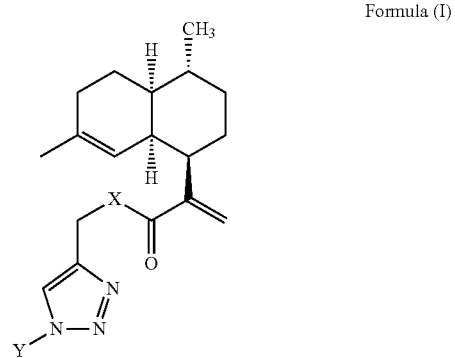

Formula (I)

Wherein,
X is selected from O or N;
Y is selected from various protected or free sugars like D-Glucose, D-Galactose, L-Rhamnose, Maltose, D-Glucal, D-Galactal, Lactose, arabinose, D-galactosamine, D-glucosamine, D-mannosamine, D-mannose, D-Xylose, D-fucose or the like.

In preferred embodiment, the artemisinic acid glycoconjugate compound of formula (I) is selected from the group consist of:
a) (2R,3S,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (4);
b) (2R,3S,4S,5R,6R)-2-((benzoyloxy)methyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl tribenzoate (5);
c) (2R,3R,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (6);
d) (2R,3R,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (7);
e) (2R,3S,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (8);

f) (2R,3R,4S,5R,6R)-2-((benzoyloxy)methyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl tribenzoate (9) and g) (2R,3R,4R,5S,6S)-2-(4-(((2-((1R,4R,4aS,8aR)-4,7-Dimethyl-1,2,3,4,4a,5,6,8a-octahydronaphthalen-1-yl)acryloyl)oxy)methyl)-1H-1,2,3-triazol-1-yl)-6-methyltetrahydro-2H-pyran-3,4,5-triyl triacetate (10).

The present invention also provides a process for the synthesis of compound of formula (I) comprising the steps of:

a) reacting artemisinic acid with propargyl alcohol or propargyl amine to afford acrylate (2) or acrylamide (3) respectively and b) subjecting the acrylate (2) or acrylamide (3) of step (a) to 1,3-dipolar cycloaddition with sugar-azides to afford compound of formula (I).

In an embodiment said step (a) comprises stirring the reaction mixture of artemisinic acid, propargyl alcohol and 4-Dimethylaminopyridine (DMAP) in a solvent at a temperature of 0° C. for a period in the range of 1 to 2 hrs followed by further stirring the reaction mixture at a temperature in the range of 25 to 30° C. for a period in the range of 10 to 12 hrs to afford corresponding acrylate compound (2).

In another embodiment said step (a) comprises adding propargyl amine to the reaction mixture of artemisinic acid, (1-[Bis(dimethylamino)methylene]-1H-1,2,3-triazolo[4,5-b]pyridinium 3-oxid hexafluorophosphate) {HATU}, N,N-Diisopropylethylamine (DIPEA) in a solvent at a temperature in the range of 25 to 30° C. followed by stirring the reaction mixture at temperature in the range of 25 to 30° C. for the period in the range of 5 to 7 hrs to afford corresponding acrylamide compound (3).

In an embodiment said step (b) comprises adding N,N-Diisopropylethylamine (DIPEA) and Copper(I) iodide (CuI) to the reaction mixture of sugar-azide and acrylate compound 2 or acrylamide compound 3 in a solvent followed by stirring the reaction mixture at a temperature in the range of 25 to 30° C. for a period in the range of 8 to 10 hrs to afford compound of formula (I).

In an embodiment said sugar-azides are protected or free sugar azides, selected from azides of D-Glucose, D-Galactose, L-Rhamnose, Maltose, D-Glucal, D-Galactal, Lactose, arabinose, D-galactosamine, D-glucosamine, D-mannosamine, D-mannose, D-Xylose or D-fucose.

In a preferred embodiment the said sugar-azide are selected from the group consisting of D-Glucosyl azide, D-Galactosyl azide, L-Rhamnosyl azide, Maltosyl azide, D-Glucal azide, Lactosyl azide and D-mannose azide.

In an embodiment the solvents used for step a and b are selected from dichloromethane, dimethylformamide, tetrahydrofuran, chloroform or carbon tetrachloride.

In yet another embodiment, the present invention provides a pharmaceutical composition comprising artemisinic acid glycoconjugate compound of formula (I) and at least one pharmaceutically acceptable carrier.

In an embodiment the present invention provides a pharmaceutical composition comprising compound of formula (I) or pharmaceutically acceptable salt thereof and pharmaceutically acceptable carrier for preventing and treating cancer or fungal infection comprising administering an effective dose of the pharmaceutical composition to a mammal.

DETAILED DESCRIPTION OF THE INVENTION

The invention will now be described in detail in connection with certain preferred and optional embodiments, so that various aspects thereof may be more fully understood and appreciated.

In view of the above, the present invention provides an artemisinic acid glycoconjugate compound of formula (I) and a process for the synthesis thereof by using 1,3-dipolar cycloaddition chemistry starting from artemisinic acid.

In an embodiment, the present invention provides an artemisinic acid glycoconjugate compound of formula (I);

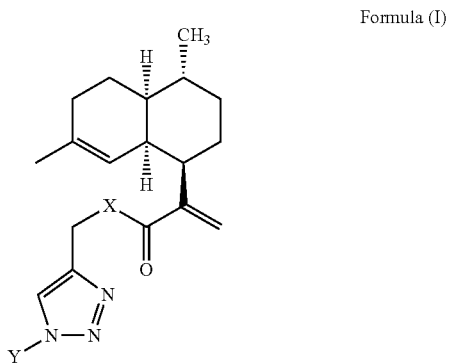

Formula (I)

Wherein,
X is selected from O or N;
Y is selected from various protected or free sugars like D-Glucose, D-Galactose, L-Rhamnose, Maltose, D-Glucal, D-Galactal, Lactose, arabinose, D-galactosamine, D-glucosamine, D-mannosamine, D-mannose, D-Xylose, D-fucose or the like.

In preferred embodiment, the artemisinic acid glycoconjugate compound of formula (I) is selected from a) (2R,3S,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (4);

b) (2R,3S,4S,5R,6R)-2-((benzoyloxy)methyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl tribenzoate (5);

c) (2R,3R,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (6);

d) (2R,3R,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (7);

e) (2R,3S,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (8); or f) (2R,3R,4S,5R,6R)-2-((benzoyloxy)methyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl tribenzoate (9) and g) (2R,3R,4R,5S,6S)-2-(4-(((2-((1R,4R,4aS,8aR)-4,7-Dimethyl-1,2,3,4,4a,5,6,8a-octahydronaphthalen-1-yl)acryloyl)oxy)methyl)-1H-1,2,3-triazol-1-yl)-6-methyltetrahydro-2H-pyran-3,4,5-triyl triacetate (10).

4

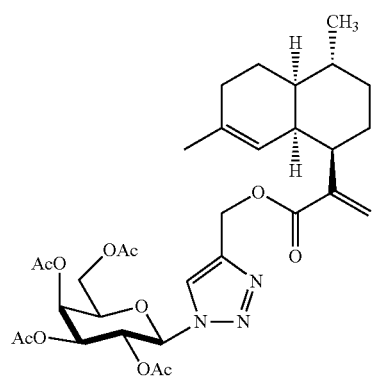

5

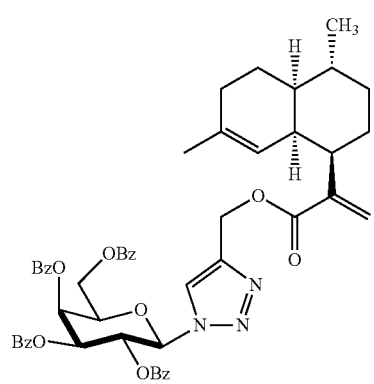

6

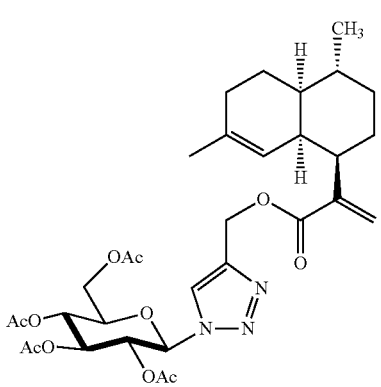

7

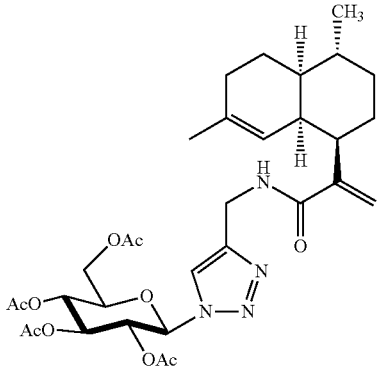

-continued

8

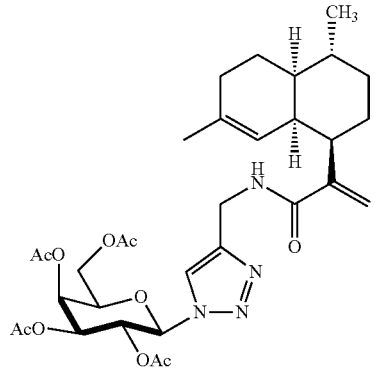

9

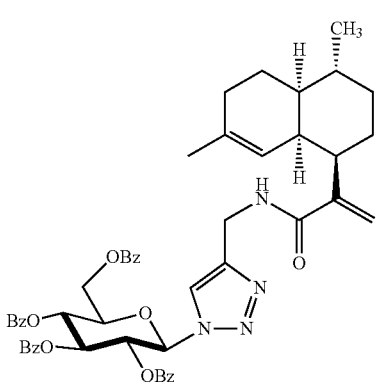

10

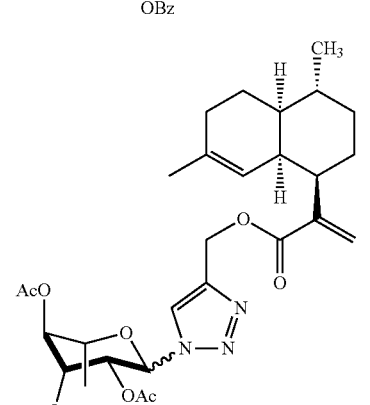

The present invention provides a method for the preparation of 12-O-artemisinic acid glycoconjugates and 12-N-artemisinic acid glycoconjugates by using 1,3-dipolar cycloaddition chemistry starting from artemisinic acid. First the artemisinic acid is propargylated and subjected to 1, 3-dipolar cycloaddition reaction with various sugar azides to furnish the desired title compounds.

In one embodiment of the present invention, the present invention provides a process for the synthesis of artemisinic acid glycoconjugate compound of formula (I) comprising the steps of:
a) Reacting artemisinic acid with propargyl amine or propargyl alcohol to afford acrylate (2) or acrylamide (3) and
b) Subjecting the acrylate (2) or acrylamide (3) of step (a) to 1, 3-dipolar cycloaddition with sugar-azides to afford compound of formula (I).

In preferred embodiment, the step (a) comprises stirring the reaction mixture of artemisinic acid, propargyl alcohol and 4-Dimethylaminopyridine (DMAP) in a solvent at a temperature 0° C. for a period in the range of 1 to 2 hrs followed by further stirring the reaction mixture of at temperature in the range of 25 to 30° C. for a period in the range of 10 to 12 hrs to afford corresponding acrylate compound (2).

In another preferred embodiment, the step (a) comprises adding propargyl amine to the reaction mixture of artemisinic acid, (1-[Bis(dimethylamino)methylene]-1H-1,2,3-triazolo[4,5-b]pyridinium 3-oxid hexafluorophosphate) {HATU}, N,N-Diisopropylethylamine (DIPEA) in a solvent at a temperature in the range of 25 to 30° C. followed by In more preferred embodiment, the sugar-azide is selected from D-Glucosyl azide, D-Galactosyl azide, L-Rhamnosyl azide, Maltosyl azide, D-Glucal azide, Lactosyl azide and D-mannose.

In one embodiment of the present invention, the reaction steps (a) and (b) are carried out under argon atmosphere.

The solvents of step (a) or (b) are selected from dichloromethane, dimethylformamide, tetrahydrofuran, chloroform or carbon tetrachloride.

The process for the synthesis of compound of formula (I) is as depicted in scheme in below:

Scheme: 1

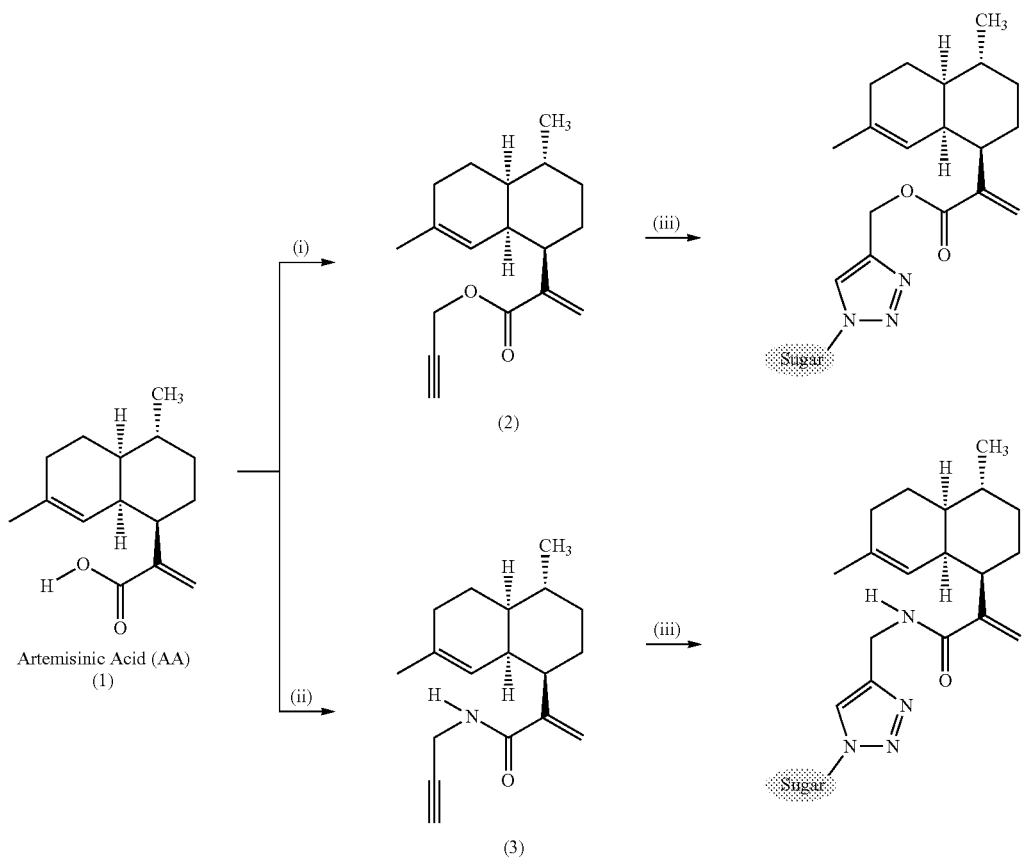

Reagents and conditions: (i) Propargyl alcohol, EDC•HCl (1.2 equiv), DMAP, (0.1 equiv), Dry DCM, 0° C. to 25° C., 12 h, 94%; (ii) Propargyl amine, HATU (1.2 equiv), DIPEA (1.2 equiv), Dry DMF, 6 h, 95%; (iii) Sugar-N₃, CuI, DIPEA, Dry DCM, 25° C., 8 to 10 h.

stirring the reaction mixture at a temperature in the range of 25 to 30° C. for a period in the range of 5 to 7 hrs to afford corresponding acrylamide compound (3).

In one embodiment of the present invention, the step (b) comprises adding N,N-Diisopropylethylamine (DIPEA) and Copper(I) iodide (CuI) to the reaction mixture of sugar-azide and acrylate compound 2 or acrylamide compound 3 in a solvent followed by stirring the reaction mixture at a temperature in the range of 25 to 30° C. for a period in the range of 8 to 10 hrs to afford compound of formula (I).

In preferred embodiment, the sugar-azide is selected from various protected or free sugar azides like D-Glucose, D-Galactose, L-Rhamnose, Maltose, D-Glucal, D-Galactal, Lactose, arabinose, D-galactosamine, D-glucosamine, D-mannosamine, D-mannose, D-Xylose and D-fucose.

The scheme 1 shows the process for the synthesis of compound of formula (I), wherein the sugar is selected from various protected or free sugars like D-Glucose, D-Galactose, L-Rhamnose, Maltose, D-Glucal, D-Galactal, Lactose, arabinose, D-galactosamine, D-glucosamine, D-mannosamine, D-mannose, D-Xylose, D-fucose or the like.

In yet another embodiment, the present invention provides a pharmaceutical composition comprising artemisinic acid glycoconjugate compound of formula (I) or pharmaceutically acceptable salt thereof and at least one pharmaceutically acceptable carrier.

The carrier is typically used when the composition is prepared, and includes, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybezoate, talcum, magnesium stearate, mineral oil, or the like.

The composition can additionally comprise stability improving material, viscosity improving or adjusting material, solubility improving material, sweetener, dye, palatability improving material, osmotic pressure variable salt, buffer solution, antioxidant, and so on.

The pharmaceutical compositions of the present invention can be oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. For parenteral administration in an aqueous solution, for example, the solution should be suitably buffered if necessary and the liquid diluent first rendered isotonic with sufficient saline or glucose.

In the present invention, the pharmaceutically acceptable salt can include a pharmaceutically acceptable acid addition salt. The pharmaceutically acceptable acid addition salt can be obtained from inorganic acids such as hydrochloric acid, nitric acid, sulfuric acid, hydrobromic acid, hydriodic acid, nitrous acid, or phosphorous acid, and nontoxic organic acids such as aliphatic mono- and di-carboxylates, phenyl-substituted alkanoate, hydroxyl alkanoate, and alkandioate, aromatic acids, and aliphatic and aromatic sulfuric acids.

In another embodiment, the present invention provides a pharmaceutical composition comprising compound of formula (I) or pharmaceutically acceptable salt thereof for preventing and treating cancer or fungal infection comprising administering an effective dose of the pharmaceutical composition to a mammal.

Further, the present invention provides a method of treating cancer or fungal infection, which is characterized by administering an effective dose of pharmaceutical composition to a mammal.

Typically, the inventive pharmaceutical composition is administered in the form of a unit dose containing its effective ingredient at an amount between about 1 mg and about 500 mg. The total dose per day of the inventive pharmaceutical composition is within a range from about 1 mg to about 500 mg, and preferably from about 1 mg to about 300 mg. However, in comprehensive consideration of the situation of a patient, and in consideration of the activity of an administered medication, a specific dose beyond such a range can be administered. An optimal dose administered under a specific situation must be decided experimentally.

The inventive compounds can be administered once or several times at a dose. Preferably, a dose per day is administered once or twice per day. The inventive compounds can be administered alone or in conjunction with a pharmaceutically acceptable carrier and excipient. The inventive pharmaceutical composition can be formulated into excipient known in the art as well as a pharmaceutically acceptable carrier and diluents. This formulation can take the form of a unit dose by a method known in the pharmaceutical field for convenience.

The inventive pharmaceutical composition can be used in conjunction with one or more other therapeutically useful materials, for instance other anti-cancer or anti-malarial drugs.

In one embodiment of the present invention provides use of artemisinic acid glycoconjugate compound of formula (I) as anti-cancer agent, anti-fungal agent, anti-malarial agent, antipyretic agent, antibacterial agent, or imaging agent. Further, the present invention provides artemisinic acid glycoconjugate compound of formula (I) which shows allelopathy effect or anti-adipogenesis effect.

In still another embodiment, the present invention provides study of anticancer activity of compound (I) against MCF-7 (breast cancer cell line) with a $IC_{50}$ value. In preferred embodiment, compound (2R,3R,4R,5S,6S)-2-(4-(((2-((1R,4R,4aS,8aR)-4,7-Dimethyl-1,2,3,4,4a,5,6,8a-octahydronaphthalen-1-yl)acryloyl)oxy)methyl)-1H-1,2,3-triazol-1-yl)-6-methyltetrahydro-2H-pyran-3,4,5-triyl triacetate (10) shows anticancer activity against MCF-7 (breast cancer cell line) with a $IC_{50}$ value of 42+/−4 µM.

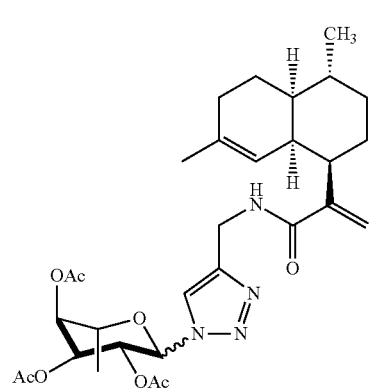

10

Many compounds of formula (I) are prepared and studied anticancer activities of these compounds against MCF7 (breast cancer cell line). Results of anticancer activities are summarized in below Table 1.

TABLE 1

In vitro anticancer activities of glycoconjugates against MCF7 (breast cancer cell line).

| Compound code | Compound | IC50 µmol |
|---|---|---|
| KTK-PA-1 | | >100 |
| KTK-PA-2 | 7 | >100 |

TABLE 1-continued

In vitro anticancer activities of glycoconjugates against MCF7 (breast cancer cell line).

| Compound code | Compound | IC50 μmol |
|---|---|---|
| KTK-PA-3 | 8 | >100 |
| KTK-PA-4 | 9 | >100 |
| KTK-PA-5 |  | >100 |
| KTK-PA-6 |  | >100 |
| KTK-PA-7 |  | >100 |
| KTK-PA-8 |  | >100 |
| KTK-PA-9 |  | >100 |
| KTK-PA-10 |  | >100 |
| KTK-PA-11 |  | >100 |
| KTK-PA-12 |  | >100 |
| KTK-AA-1 |  | >100 |
| KTK-AA-2 | 4 | >100 |
| KTK-AA-3 |  | >100 |
| KTK-AA-4 | 6 | >100 |
| KTK-AA-5 |  | >100 |
| KTK-AA-6 | 5 | >100 |
| KTK-AA-7 | 10 | 42 ± 2 |
| KTK-AA-8 |  | >100 |
| KTK-AA-9 |  | >100 |
| KTK-AA-10 |  | >100 |
| KTK-AA-11 |  | >100 |
| KTK-AA-12 |  | >100 |
| KTK-AA- Artimisinic acid | 1 | >100 |

From table 1, it is observed that compound 10 shows unexpected enhancement in anticancer activity over artimisinic acid, IC50 value is more than 50% less when compared with artimisinic acid, thus providing very potent anticancer activity against breast cancer cell lines. Further, a library of compounds of formula (I) are undergoing screening and testing against more cell lines for various pharmacological activities.

In one embodiment, the present invention provides a method for treating cancer or fungal infection, wherein said method comprises administering to the subject a therapeutically effective amount of artemisinic acid glycoconjugate compound of formula (I) or pharmaceutically acceptable salt thereof.

EXAMPLES

Following examples are given by way of illustration therefore should not be construed to limit the scope of the invention.

Example 1: Synthesis of prop-2-yn-1-yl 2-((1R,4R,4aS,8aR)-4,7-dimethyl-1,2,3,4,4a,5,6,8a-octahydronaphthalen-1-yl)acrylate (2)

A solution of Artemisinic acid (AA) (325 mg, 1 equiv), propargyl alcohol (80 μL, 1 equiv.) and DMAP (17 mg, 0.1 equiv) in a dry DCM (5 mL) was cooled to 0° C. and then treated with EDC.HCl (1.2 equiv). The reaction mixture was stirred at the same temperature (0° C.) for 2 h and then at 25° C. for a 10 h. After completion of reaction (TLC), the reaction mixture concentrated in vacuo, the residue was taken up in EtOAc and water. The organic layers were collected and washed with saturated $NH_4Cl$ solution, and dried over $Na_2SO_4$. The solvent was concentrated in vacuo and subjected to flash chromatography to give compound 2 (354 mg) in 94% yield.

$^1$H NMR (CHLOROFORM-d, 500 MHz): δ=6.35 (s, 1H), 5.49 (s, 1H), 4.97 (br. s, 1H), 4.78-4.68 (m, 2H), 2.73-2.69 (m, 1H), 2.50-2.57 (m, 1H), 2.47-2.46 (m, 1H), 1.94-1.83 (m, 2H), 1.78-1.67 (m, 2H), 1.58 (s, 3H), 1.55-1.49 (s, 1H), 1.45-1.30 (m, 4H), 1.10-1.02 (m, 1H), 0.89 (d, J=5.7 Hz, 3H). $^{13}$C NMR (CHLOROFORM-d, 126 MHz): δ=166.3, 142.6, 134.9, 125.2, 120.2, 77.8, 74.8, 52.1, 42.3, 41.3, 37.9, 35.2, 27.5, 26.4, 25.9, 25.5, 23.7, 19.7. HRMS (ESI) m/z found 295.1661 [M+Na]$^+$ (calcd for $C_{18}H_{24}O_2Na$, 295.1669).

Example 2: Synthesis of 2-((1R,4R,4aS,8aR)-4,7-dimethyl-1,2,3,4,4a,5,6,8a-octahydronaphthalen-1-yl)-N-(prop-2-yn-1-yl)acrylamide (3)

To a solution of artemisinic acid (1), (100 mg, 1 equiv), HATU (191 mg, 1.2 equiv) and DIPEA (87 μL, 1.2 equiv) in DMF (10 mL) was added propargyl amine (32 μL, 1.2 equiv) at 25° C. under a argon atmosphere. The mixture was stirred for 6 h. After completion of reaction (TLC), the solvent was removed in vacuo and the resulting oil residue was diluted with DCM (15 mL) and extracted with water. The combined DCM layers were dried over $Na_2SO_4$ filtered and concentrated. The crude product was purified by flash chromatography to give compound 3 (109 mg) in 95% yield.

$^1$H NMR (500 MHz, $CDCl_3$) δ=6.29 (brs, 1H), 5.63 (s, 1H), 5.15 (s, 1H), 4.96 (s, 1H), 4.16-4.11 (m, 1H), 4.03-3.98 (m, 1H), 2.74 (d, J=12.6 Hz, 1H), 2.42 (s, 1H), 2.23 (t, J=2.7 Hz, 1H), 2.15 (s, 1H), 1.90-1.85 (m, 2H), 1.75-1.66 (m, 2H), 1.57 (s, 3H), 1.56-1.49 (m, 1H), 1.44-1.37 (m, 3H), 1.29-1.23 (m, 1H), 0.86 (d, J=5.3 Hz, 3H). $^{13}$C NMR (125 MHz, $CDCl_3$) δ=169.5, 148.7, 135.1, 120.2, 116.6, 79.6, 71.6, 42.6, 41.2, 37.7, 35.0, 29.4, 27.5, 26.4, 25.4, 25.3, 23.7, 19.7. HRMS (ESI): m/z calcd for [M+H]$^+$, $C_{18}H_{26}ON$ 272.2009 found 272.2004.

Example 3: General Procedure for the Synthesis of Artemisinic Acid Glycoconjugates To a stirred solution of various sugar-azides (1 equiv) and compound 2 (1 equiv) or compound 3 (1 equiv) in a dry DCM (5 mL), DIPEA (1 equiv) and CuI (0.5 equiv) were added under argon atmosphere. The solution was stirred at 25° C. for 8 to 10 h. After completion of the reaction (TLC), the reaction mixture diluted with DCM (10 mL) and washed with water, the DCM layer dried over anhydrous $Na_2SO_4$, concentrated in vacuo. The crude residue was subjected to flash chromatography to give various artemisinic glycoconjugates in excellent yields (85-98%).

I. (2R,3S,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (4)

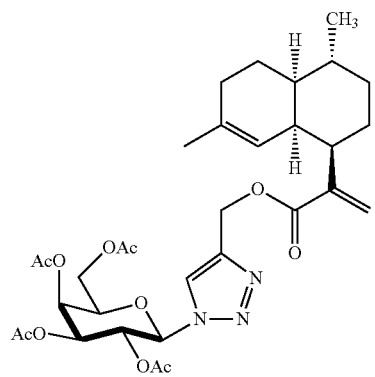

To a stirred solution of various galactosyl azide (1 equiv) and compound 2 (1 equiv) in a dry DCM (5 mL), DIPEA (1 equiv) and CuI (0.5 equiv) were added under argon atmosphere. The solution was stirred at 25° C. for 10 h. After completion of the reaction (TLC), the reaction mixture diluted with DCM (10 mL) and washed with water, the DCM layer dried over anhydrous $Na_2SO_4$, concentrated in vacuo. The crude residue was subjected to flash chromatography to give artemisinic glycoconjugates in excellent yields (94%).

II. (2R,3S,4S,5R,6R)-2-((benzoyloxy)methyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl tribenzoate (5)

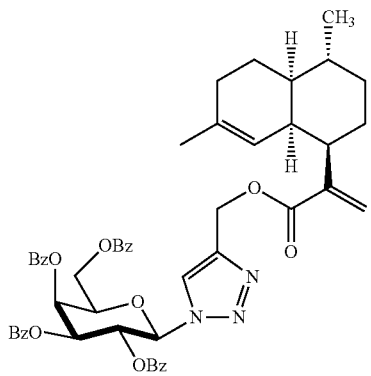

$^1$H NMR (400 MHz, $CDCl_3$): δ=8.14-8.12 (m, 3H), 8.02-8.00 (m, 2H), 7.81-7.77 (m, 4H), 7.70-7.66 (m, 1H), 7.58-7.54 (m, 3H), 7.47-7.40 (m, 4H), 7.32-7.24 (m, 4H), 6.32-6.18 (m, 4H), 5.91-5.88 (m, 1H), 5.47 (br s, 1H), 5.39 (d, J=12.8 Hz, 1H), 5.24 (d, J=12.8 Hz, 1H), 5.01 (br. s., 1H), 4.72-4.64 (m, 2H), 4.53-4.49 (m, 1H), 2.74-2.71 (m, 1H), 2.58 (br. s., 1H), 1.90-1.69 (m, 5H), 1.59 (br. s., 3H), 1.55-1.50 (m, 1H), 1.43-1.36 (m, 4H), 0.89 (d, J=4.5 Hz, 3H); $^{13}$C NMR (100 MHz, $CDCl_3$): δ=167.0, 166.0, 165.4, 165.3, 164.8, 142.8, 134.9, 133.9, 133.7, 133.5, 133.4, 129.9, 129.8, 129.7, 129.1, 128.9, 128.8, 128.5, 128.4, 128.1, 125.1, 120.3, 86.5, 74.7, 71.7, 68.8, 68.0, 62.0, 57.6, 42.3, 41.4, 38.0, 35.2, 27.6, 26.4, 25.9, 25.6, 23.7, 19.7; HRMS (ESI): m/z: calcd for [M+Na]$^+$, $C_{52}H_{51}O_{11}N_3Na$ 916.3416 found 916.3408.

$^1$H NMR (400 MHz, $CDCl_3$): δ=7.90 (s, 1H), 6.30 (s, 1H), 5.84 (d, J=9.2 Hz, 1H), 5.54-5.49 (m, 2H), 5.44 (s, 1H), 5.33-5.30 (m, 1H), 5.26-5.17 (m, 2H), 4.94 (br. s., 1H), 4.24-4.16 (m, 2H), 4.12-4.08 (m, 2H), 2.67 (d, J=11.0 Hz, 1H), 2.51 (br. s., 1H), 2.19 (s, 3H), 2.00 (s, 3H), 1.97 (s, 3H), 1.89-1.87 (m, 1H), 1.82 (s, 3H), 1.72-1.64 (m, 2H), 1.54 (br. s., 3H), 1.38-1.28 (m, 3H), 1.26-1.19 (m, 3H), 0.85 (d, J=4.9 Hz, 3H); $^{13}$C NMR (100 MHz, $CDCl_3$): δ=170.3, 170.0, 169.8, 168.9, 166.9, 143.6, 142.7, 134.8, 125.2, 122.5, 120.2, 86.2, 74.0, 70.7, 67.8, 66.9, 61.2, 60.3, 57.5, 42.3, 41.3, 37.9, 35.2, 27.5, 26.3, 25.9, 25.5, 23.6, 20.6, 20.4, 20.1, 19.7; HRMS (ESI): m/z calcd for [M+H]$^+$, $C_{32}H_{44}O_{11}N_3$ 646.3699 found 646.2970.

III. (2R,3R,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (6)

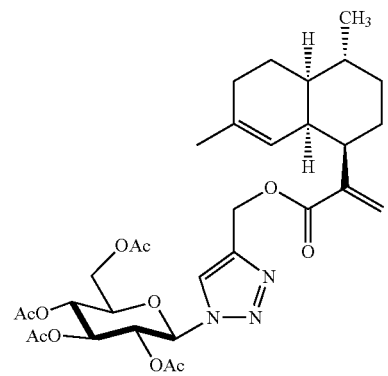

$^1$H NMR (500 MHz, $CDCl_3$): δ=7.84 (s, 1H), 6.27 (s, 1H), 5.89-5.87 (m, 1H), 5.42-5.39 (m, 3H), 5.28-5.18 (m, 3H), 4.92 (br. s., 1H), 4.28-4.24 (m, 1H), 4.12-4.09 (m, 1H), 4.02-3.99 (m, 1H), 2.65 (d, J=11.8 Hz, 1H), 2.49 (br. s., 1H), 2.03 (s, 3H), 2.01 (s, 3H), 1.97 (s, 3H), 1.83-1.80 (m, 4H), 1.71-1.63 (m, 3H), 1.52 (br. s., 3H), 1.37-1.27 (m, 4H), 1.18-1.23 (m, 2H), 0.83 (d, J=5.7 Hz, 3H); $^{13}$C NMR (125 MHz, $CDCl_3$): δ=170.5, 169.9, 169.3, 168.7, 166.9, 143.7, 142.7, 134.8, 125.1, 122.2, 120.2, 85.6, 75.1, 72.6, 70.3, 67.7, 61.5, 57.5, 42.3, 41.3, 37.9, 35.2, 29.6, 27.5, 26.3, 25.8, 25.5, 23.6, 20.6, 20.5, 20.0, 19.7; HRMS (ESI) m/z: calcd for [M+Na]$^+$, $C_{32}H_{43}O_{11}N_3Na$ 668.2790 found 668.2880.

IV. (2R,3R,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (7)

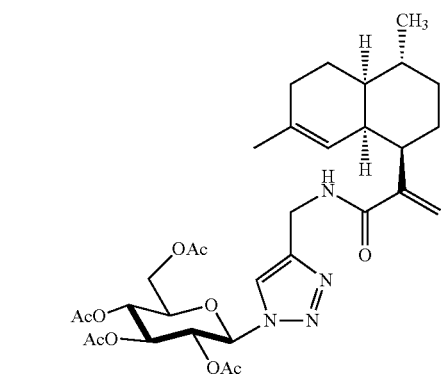

¹H NMR (500 MHz, CDCl₃) δ=7.81 (s, 1H), 6.81 (m, 1H), 5.86 (d, J=8.8 Hz, 1H), 5.59 (s, 1H), 5.43-5.38 (m, 2H), 5.21 (t, J=9.5 Hz, 1H), 5.13-5.10 (m, 1H), 4.98 (br. s., 1H), 4.59 (dd, J=15.3, 6.1 Hz, 1H), 4.48 (dd, J=15.3, 5.7 Hz, 1H), 4.26 (dd, J=12.6, 5.0 Hz, 1H), 4.14-4.06 (m, 1H), 4.03-4.00 (m, 1H), 2.77-2.72 (m, 1H), 2.44 (br. s., 1H), 2.05 (s, 3H), 2.03 (s, 3H), 1.99 (s, 3H), 1.91-1.86 (m, 2H), 1.81 (s, 3H), 1.76-1.72 (m, 1H), 1.68-1.66 (m, 1H), 1.56 (s, 3H), 1.40-1.37 (m, 3H), 1.25-1.22 (m, 2H), 0.85 (d, J=5.7 Hz, 3H); ¹³C NMR (125 MHz, CDCl₃) δ=170.5, 169.9, 169.3, 168.7, 148.8, 145.6, 135.1, 121.0, 120.3, 116.4, 85.7, 75.0, 72.6, 70.5, 67.7, 61.5, 42.5, 41.2, 37.8, 35.0, 34.9, 27.5, 26.4, 25.5, 25.2, 23.7, 20.6, 20.5, 20.4, 20.1, 19.7; HRMS (ESI) m/z: calcd for [M+H]⁺, $C_{32}H_{45}O_{10}N_4$ 645.3130 found 645.3109.

V. (2R,3S,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (8)

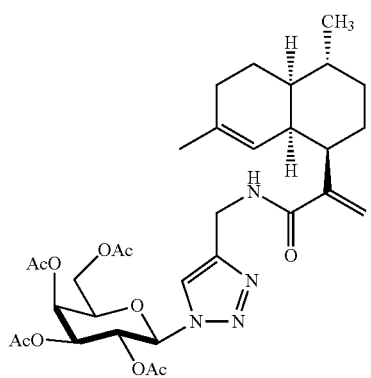

¹H NMR (500 MHz, CDCl₃) δ=7.86 (s, 1H), 6.82-6.81 (m, 1H), 5.83 (d, J=9.2 Hz, 1H), 5.60 (s, 1H), 5.52-5.48 (m, 2H), 5.26 (dd, J=10.3, 3.0 Hz, 1H), 5.12 (s, 1H), 4.97 (br. s., 1H), 4.66 (dd, J=15.3, 6.3 Hz, 1H), 4.39 (dd, J=15.3, 5.3 Hz, 1H), 4.25 (t, J=6.5 Hz, 1H), 4.20-4.16 (m, 1H), 4.13-4.06 (m, 1H), 2.77-2.72 (m, 1H), 2.43 (br. s., 1H), 2.20 (s, 3H), 2.01 (s, 3H), 1.98 (s, 3H), 1.89-1.85 (m, 2H), 1.83 (s, 3H), 1.73-1.65 (m, 2H), 1.55 (s, 3H), 1.42-1.37 (m, 3H), 1.28-1.22 (m, 2H), 0.85 (d, J=5.3 Hz, 3H); ¹³C NMR (125 MHz, CDCl₃) δ=170.3, 170.1, 169.8, 168.9, 148.7, 145.2, 135.0, 121.2, 120.3, 116.5, 86.2, 74.0, 70.7, 68.0, 66.9, 61.2, 42.5, 41.2, 37.8, 35.0, 34.8, 27.5, 26.4, 25.4, 25.3, 23.7, 20.6, 20.6, 20.5, 20.1, 19.7; HRMS (ESI) m/z: calcd for [M+H]⁺, $C_{32}H_{45}O_{10}N_4$ 645.3130 found 645.3113.

VI. (2R,3R,4S,5R,6R)-2-((benzoyloxy)methyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl tribenzoate (9)

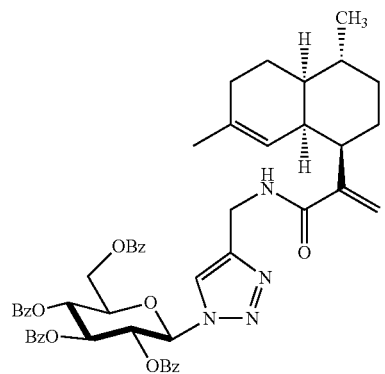

¹H NMR (400 MHz, CDCl₃) δ=8.01-7.98 (m, 3H), 7.93-7.91 (m, 2H), 7.82-7.80 (m, 2H), 7.76-7.74 (m, 2H), 7.53-7.48 (m, 2H), 7.43-7.33 (m, 6H), 7.29-7.25 (m, 4H), 6.68 (s, 1H), 6.29 (d, J=9.2 Hz, 1H), 6.15 (t, J=9.5 Hz, 1H), 5.99-5.94 (m, 1H), 5.89-5.84 (m, 1H), 5.54 (s, 1H), 5.08 (s, 1H), 5.01 (s, 1H), 4.64-4.63 (m, 2H), 4.52-4.49 (m, 3H), 2.79-2.78 (m, 2H), 2.49 (s, 1H), 2.03 (s, 1H), 1.91-1.85 (m, 2H), 1.70-1.67 (m, 1H), 1.59 (s, 3H), 1.40 (m, 2H), 1.26-1.23 (m, 2H), 0.88 (d, J=4.9 Hz, 3H); ¹³C NMR (100 MHz, CDCl₃) δ=169.9, 166.1, 165.6, 165.1, 164.6, 148.8, 135.1, 133.7, 133.6, 133.5, 133.3, 129.9, 129.8, 129.7, 129.3, 128.5, 128.4, 128.3, 128.0, 121.1, 120.3, 116.4, 86.1, 75.5, 73.0, 71.2, 68.9, 62.8, 42.6, 41.2, 38.6, 37.8, 35.0, 27.6, 26.4, 25.4, 25.3, 23.7, 19.7; HRMS (ESI) m/z: calcd for [M+H]⁺, $C_{52}H_{53}O_{10}N_4$ 893.3756 found 893.3749.

VII. (2R,3R,4R,5S,6S)-2-(4-(((2-((1R,4R,4aS,8aR)-4,7-Dimethyl-1,2,3,4,4a,5,6,8a-octahydronaphthalen-1-yl)acryloyl)oxy)methyl)-1H-1,2,3-triazol-1-yl)-6-methyltetrahydro-2H-pyran-3,4,5-triyl triacetate (10)

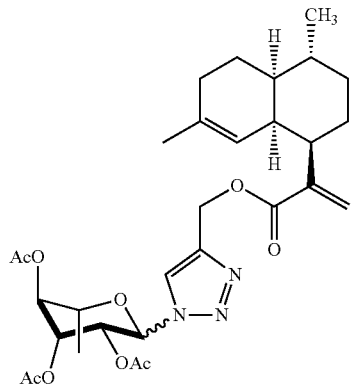

Colorless solid; Yield: 90%, m.p.: 89-92° C.; Rf=0.40 (40% EtOAc-petroleum ether); flash chromatography eluting with 25% EtOAc-petroleum ether; [α]D26=+26.62 (c 1.7, CHCl₃); 1H NMR (500 MHz, CDCl₃): δ=7.84 (s, 1H), 6.30-6.27 (m, 1H), 6.14 (s, 1H), 5.95-5.80 (m, 1H), 5.66-5.65 (m, 1H), 5.45-5.43 (m, 1H), 5.34-5.29 (m, 1H), 5.23-5.20 (m, 1H), 5.18-5.15 (m, 1H), 4.92 (s, 1H), 3.86-3.81 (m, 1H), 2.69-2.64 (m, 1H), 2.49 (brs, 1H), 2.14 (s, 1H), 2.06 (s, 3H), 2.03-2.01 (m, 4H), 1.95 (s, 3H), 1.91-1.82 (m, 2H), 1.74-1.65 (m, 2H), 1.55 (s, 3H), 1.39-1.38 (m, 2H), 1.32 (d, J=6.5 Hz, 3H), 1.22-1.20 (m, 2H), 0.86 (d, J=5.3 Hz, 3H); $^{13}$C NMR (125 MHz, CDCl$_3$): δ=169.8, 169.8, 169.1, 167.0, 143.6, 142.9, 142.7, 142.7, 134.9, 125.2, 125.1, 124.0, 123.1, 120.1, 120.1, 84.6, 83.8, 73.9, 70.7, 70.0, 69.6, 69.2, 68.8, 68.4, 60.3, 57.6, 57.5, 42.3, 41.4, 41.3, 37.9, 35.2, 27.5, 26.3, 25.8, 25.5, 23.6, 20.7, 20.5, 20.5, 20.3, 19.7, 17.5, 17.1, 14.1; HRMS (ESI) m/z: calcd for C$_{30}$H$_{42}$O$_9$N$_3$ [M+H]$^+$: 588.2916, found 588.2903

Example 4: Study of Anticancer Activity Against MCF-7 (Breast Cancer Cell Line)

Methodology

Compounds were dissolved in DMSO (Sigma) to prepare 50 mM concentrations stock solutions. All the further dilutions were also made in DMSO. During the treatment, the final concentration of DMSO was maintained <0.02%.

Antibodies

Anti-Caspase 9 and Anti-Caspase 3 antibodies were purchased from Cell Signaling and Anti-αTubulin antibody was procured from Sigma, Goat anti-rabbit HRP conjugated secondary antibody was purchased from Bio-Rad, and Goat anti-mouse HRP conjugated secondary antibody was purchased from Cell Signaling.

Cell Culture

Breast cancer cell line MCF7, maintained at NCCS, a national resource for providing cell lines, was grown in DMEM (GIBCO), MBA-MB-231 in RPMI (GIBCO) with 10% FBS, 100 U/mL penicillin and 100 μg/mL streptomycin and MCF10A in DMEM/F12 (Gibco) containing, horse Serum (10% final), EGF (20 ng/ml), Hydrocortisone (0.5 mg/ml), Cholera Toxin (100 ng/ml), Insulin (10 μg/ml) and Penicillin/Streptomycin mix (1 ml/100 ml) at 37° C. in a humid, 5% CO$_2$ regulated incubator.

Growth Inhibition by Cytotoxicity Assay

The cytotoxic effect of the compounds was determined using MTT (3-(4, 5 dimethylthiazol-2-yl)-2-5 diphenyltetrazolium bromide) assay. Cells were seeded (4×10$^3$ per well) in 96 well plates. After 24 hours of seeding, cells were exposed with varying concentrations (0-100 M) of respective compounds for 48 hours in triplicates. Then, MTT solution (20 μL of 5 mg/mL stock for each well of 96 well plate) was added and further incubated for 3.5 hours in humid 5% CO$_2$ incubator. Media containing MTT solution was then replaced by MTT solvent (iso-propanol, HCl and Triton X-100), incubated for 15 min at room temperature with gentle shaking for complete dissolution of Formazan. Absorbance was measured at 570 nm using a Thermo Scientific Multiskan GO Elisa plate reader and IC 50 was calculated by routine methods. All experiments were carried out at least in triplicate, and the percentage of viable cells was calculated as the mean with respect to the controls.

Table 1 shows the results for anticancer activity.

| Compound Code | Compound | IC50 μmol |
|---|---|---|
| KTK-PA-1 | | >100 |
| KTK-PA-2 | 7 | >100 |
| KTK-PA-3 | 8 | >100 |
| KTK-PA-4 | 9 | >100 |
| KTK-PA-5 | | >100 |
| KTK-PA-6 | | >100 |
| KTK-PA-7 | | >100 |
| KTK-PA-8 | | >100 |
| KTK-PA-9 | | >100 |
| KTK-PA-10 | | >100 |
| KTK-PA-11 | | >100 |
| KTK-PA-12 | | >100 |
| KTK-AA-1 | | >100 |
| KTK-AA-2 | 4 | >100 |
| KTK-AA-3 | | >100 |
| KTK-AA-4 | 6 | >100 |
| KTK-AA-5 | | >100 |
| KTK-AA-6 | 5 | >100 |
| KTK-AA-7 | Compound 10 | 42 ± 2 |
| KTK-AA-8 | | >100 |
| KTK-AA-9 | | >100 |
| KTK-AA-10 | | >100 |
| KTK-AA-11 | | >100 |
| KTK-AA-12 | | >100 |
| KTK-AA- Artimisinic acid | 1 | >100 |

ADVANTAGES OF THE INVENTION

The present invention provide novel artemisinic acid glycoconjugate of formula (I) a which is used as anti-cancer agent, anti-malarial agent or imaging agent. The number of novel 12-O-artemisinic acid glycoconjugates and 12-N-artemisinic acid glycoconjugates are synthesized starting from artemisinic acid by a simple, environment friendly and economic process.

We claim:

1. A compound of formula (I);

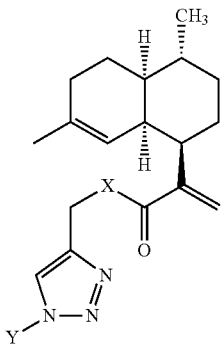

Formula (I)

wherein X is selected from O or N; and
Y is selected from D-Glucose, D-Galactose, L-Rhamnose, Maltose, D-Glucal, D-Galactal, Lactose, arabinose, D-galactosamine, D-glucosamine, D-mannosamine, D-mannose, D-Xylose, and D-fructose.

2. The compound of formula (I) as claimed in claim 1, wherein said compound of formula (I) is selected from the group consisting of
a) (2R,3S,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (4);
b) (2R,3S,4S,5R,6R)-2-((benzoyloxy)methyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl tribenzoate (5);

c) (2R,3R,4S,5R,6R)-2-(acetoxymethyl)-6-(4-(((2-((1R,4R,4aS,8aR)-4,7-dimethyl-1,2,3,4,4a,5,6,8a-octahydronaphthalen-1-yl)acryloyl)oxy)methyl)-1H-1,2,3-triazol-1-yl)tetrahydro-2H-pyran-3,4,5-triyl triacetate (6);

d) (2R,3R,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (7);

e) (2R,3S,4S,5R,6R)-2-(acetoxymethyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl triacetate (8);

f) (2R,3R,4S,5R,6R)-2-((benzoyloxy)methyl)-6-(4-((2-((1R,4R,4aS,8aR)-4,7-dimethyl-1,2,3,4,4a,5,6,8a-octahydronaphthalen-1-yl)acrylamido)methyl)-1H-1,2,3-triazol-1-yl)tetrahydro-2H-pyran-3,4,5-triyl tribenzoate (9); and g) (2R,3R,4R,5S,6S)-2-(4-(((2-((1R,4R,4aS,8aR)-4,7-Dimethyl-1,2,3,4,4a,5,6,8a-octahydronaphthalen-1-yl)acryloyl)oxy)methyl)-1H-1,2,3-triazol-1-yl)-6-methyl-tetrahydro-2H-pyran-3,4,5-triyl triacetate (10).

3. A pharmaceutical composition comprising the compound of claim 1 or pharmaceutically acceptable salt thereof and pharmaceutically acceptable carrier.

4. A process for the synthesis of compound of formula (I) comprising the steps of:
   a) reacting artemisinic acid with propargyl alcohol or propargyl amine to afford acrylate (2) or acrylamide (3) respectively; and
   b) subjecting the acrylate (2) or acrylamide (3) of step (a) to 1, 3-dipolar cycloaddition with sugar-azides to afford compound of formula (I).

5. The process as claimed in claim 4, wherein said step (a) comprises stirring the reaction mixture of artemisinic acid, propargyl alcohol and 4-Dimethylaminopyridine (DMAP) in a solvent at a temperature of 0° C. for a period in the range of 1 to 2 hrs followed by further stirring the reaction mixture at a temperature in the range of 25 to 30° C. for a period in the range of 10 to 12 hrs to afford corresponding acrylate compound (2).

6. The process as claimed in claim 4, wherein said step (a) comprises adding propargyl amine to the reaction mixture of artemisinic acid, (1-[Bis(dimethylamino)methylene]-1H-1,2,3-triazolo[4,5-b]pyridinium-3-oxid hexafluorophosphate) {HATU}, N,N-Diisopropylethylamine (DIPEA) in a solvent at a temperature in the range of 25 to 30° C. followed by stirring the reaction mixture at temperature in the range of 25 to 30° C. for the period in the range of 5 to 7 hrs to afford corresponding acrylamide compound (3).

7. The process as claimed in claim 4, wherein said step (b) comprises adding N,N-Diisopropylethylamine (DIPEA) and Copper(I) iodide (CuI) to the reaction mixture of sugar-azide and acrylate compound 2 or acrylamide compound 3 in a solvent followed by stirring the reaction mixture at a temperature in the range of 25 to 30° C. for a period in the range of 8 to 10 hrs to afford compound of formula (I).

8. The process as claimed in claim 7, wherein said sugar-azides are protected or free sugar azides, selected from azides of D-Glucose, D-Galactose, L-Rhamnose, Maltose, D-Glucal, D-Galactal, Lactose, arabinose, D-galactosamine, D-glucosamine, D-mannosamine, D-mannose, D-Xylose, and D-fucose.

9. The process as claimed in claim 8, wherein said sugar-azide are selected from the group consisting of D-Glucosyl azide, D-Galactosyl azide, L-Rhamnosyl azide, Maltosyl azide, D-Glucal azide, Lactosyl azide and D-mannose azide.

10. The process as claimed in claim 4, wherein the solvents used for step a and b are selected from dichloromethane, dimethylformamide, tetrahydrofuran, chloroform, and carbon tetrachloride.

* * * * *